United States Patent [19]

Scurlock

[11] 3,952,740

[45] Apr. 27, 1976

[54] GAS FLOW MONITOR FOR ANESTHETIC MACHINES

[75] Inventor: James E. Scurlock, Fort Devens, Mass.

[73] Assignee: The United States of America as represented by the National Institute of Health, Washington, D.C.

[22] Filed: May 12, 1975

[21] Appl. No.: 576,581

[52] U.S. Cl. .......................... 128/145.8; 128/188; 128/209; 128/142 G; 137/557
[51] Int. Cl.² ........................................ A61M 16/00
[58] Field of Search ........... 128/145.8, 145.6, 145.5, 128/188, 209, 210, 146.5; 137/557

[56] References Cited
UNITED STATES PATENTS

| | | | |
|---|---|---|---|
| 2,828,741 | 4/1958 | Delest | 128/146.5 |
| 3,171,411 | 3/1965 | Levine | 128/188 |
| 3,348,772 | 10/1967 | Chabrier et al. | 137/557 |
| 3,351,057 | 11/1967 | Goodyear et al. | 128/188 |
| 3,870,012 | 3/1975 | Metnier | 128/145.8 |
| 3,896,837 | 7/1975 | Rolling | 128/210 |

*Primary Examiner*—Robert W. Michell
*Assistant Examiner*—Henry J. Recla
*Attorney, Agent, or Firm*—Holman & Stern

[57] ABSTRACT

Disclosed is a gas flow monitor for an anesthetic machine which will alert the operator in the event of either a fall in oxygen pressure or any other event leading to an inadequate oxygen flow while other gases are being supplied. The monitor comprises a fluidic OR/NOR logic gate which receives a gaseous anesthetic under pressure as its power stream input. A respiratory gas such as oxygen, is fed to one control stream of the gate and, when an adequate flow thereof exists, a mixture of oxygen and gaseous anesthetic flows through the OR outlet port and is supplied to the breathing circuit. If an insufficient diverting flow of oxygen is present in the control stream, the gaseous anesthetic will be switched by the fluidic gate to flow through the NOR outlet which is connected to activate a pressure electric switch to sound an alarm.

8 Claims, 3 Drawing Figures

OR/NOR FLUIDIC GATE

GAS FLOW MONITOR FOR ANESTHETIC MACHINES

This invention relates to anesthesis apparatus, and more particularly relates to apparatus adapted for use with a gas anesthesia machine for the purpose of safeguarding against the loss of the oxygen flow to the patient.

BACKGROUND OF THE INVENTION

Anesthetics are drugs which produce anesthesia, a condition of inability to appreciate sensation. Two types of anesthesia are usually recognized: local anesthesia, in which the anesthesia is confined to a portion of the body and under which the patient is conscious and general anesthesia, in which the anesthesia extends to the entire body and under which the patient is unconscious, in a state of muscular relaxation and insensibility to pain. The latter type is employed for most surgical operations.

The general anesthetics may be divided into three groups: inhalation anesthetics, intravenous anesthetics, and those which are used only to induce basal anesthesia. Inhalation anesthetics include the volatile liquids and gases.

Volatile liquids and gases are commonly used to induce anesthesia by progressively increasing the amount of volatile anesthetic in the inspired air and thus in the blood and brain. The administration of an anesthetic results in progressive depression of the central nervous system, which may be preceded by varying degrees of excitation. These drugs first depress the cerebral cortex and then the basal ganglia and cerebellum. At this level, a state of analgesia is induced with a reduction of perception to painful stimuli, useful in minor surgery. This stage is followed first by sensory and then motor paralysis of the functions of the spinal cord from below, upward. This is the level at which most major surgical procedures are carried out. If the administration of the anesthetic is continued, the medullary centers are involved, and death may result from paralysis of the respiratory and vasomotor centers.

The inhalation anesthetics are usually administered by one of two methods. In the open method; the liquid anesthetic is dropped on a cotton or guaze mask held over the patient's nose or mouth. Air is the diluent and no anesthetic machine is required. In the closed method; the gaseous or liquid anesthetic is contained in a special apparatus which, when attached to the patient's nose and mouth, constitutes a closed system. The patient is continually rebreathing the contents of the system. Provision is made for the removal of carbon dioxide with soda lime and the addition of oxygen as needed. Sometimes, a semiclosed method, a modification of the second method, is used. This method employs a closed method type of apparatus, but a valve on the mask permits ready expiration outside the system, The gaseous anesthetic agents are vapors at ordinary room temperature and, in general, have boiling points at less than 20° C. Consequently, they are confined under high pressure in cylinders and administered by the closed method with an anesthetic machine. The anesthetic machine controls the mixing of the anesthetic gas with oxygen or air so as to sustain respiration while maintaining the anesthetized state of the patient. These agents vary greatly in anesthetic potency, and their successful use often depends upon reliable control of the mixture of the anesthetic gas and oxygen or air supplied to the patient. Nitrous oxide is nonirritating and causes no untoward side actions if anoxia is avoided. But to avoid anoxia, close control must be maintained over the ratio of the anesthetic agent and the oxygen or air which is blended therewith. If the relative amount of oxygen is inadvertently reduced to below 20 percent thru a spent oxygen cylinder or defective oxygen supply, or human error anoxia is certain unless some means is present to detect this malfunction and sound an alarm. These considerations obtain for other gaseous anesthetics as well, such as cyclopropane and ethylene.

In addition, the margin for error in controlling the mixture of nitrous oxide and oxygen is small, inasmuch as high concentrations of nitrous oxide are required, little room is left in the mixture for oxygen. This may result in serious anoxia and tissue damage, especially to the central nervous system. For this reason, a reliable means to monitor the gas mixture is required for the proper use of nitrous oxide as an anesthetic.

Prior art systems for monitoring oxygen flow in anesthetic machines generally comprise mechanical actuators responsive to a reduction in the oxygen supply pressure below a predetermined minimum value. These actuators are comprised of many moving parts which are subject to wear, thereby impairing their reliability. These prior art actuators are, in addition, generally bulky and inconvenient to employ in portable anesthetic machines.

OBJECTS OF THE INVENTION

It is an object of the invention to monitor the ratio of a respiratory gas to an anesthetic gas in an anesthetic machine, in an improved manner.

It is another object of the invention to monitor the ratio of a respiratory gas to an anesthetic gas in an anesthetic machine, with an apparatus having fewer moving parts than has been available in the prior art.

It is still another object of the invention to monitor the ratio of a respiratory gas to an anesthetic gas in an anesthetic machine, with an apparatus which is smaller and more compact than has been available in the prior art.

It is yet another object of the invention to monitor the ratio of a respiratory gas to an anesthetic gas in an anesthetic machine, in a more reliable manner than has been available to the prior art.

SUMMARY OF THE INVENTION

These and other objects, features, and advantages of the invention are accomplished by the gas flow monitor apparatus disclosed herein. The inventive apparatus finds application in an anesthetic machine which includes a source of pressurized anesthetic gas and a source of pressurized respiratory gas. The gas flow monitor includes a fluidic OR/NOR gate having a power stream input connected to the source of anesthetic gas and a control stream input connected to the source of respiratory gas. The fluidic gate has an OR output leg and a NOR output leg. The breathing circuit for a patient is connected to the OR output leg of the fluidic gate. The anesthetic gas and the respiratory gas are mixed in the fluidic gate and the resulting gas mixture flows through the OR output leg thereof and into the breathing circuit, when the flow rate of the respiratory gas in the control stream is sufficiently great. An alarm means is connected to the NOR output leg of the fluidic gate, for manifesting an alarm signal when a reduction in the flow rate of the respiratory gas in the control stream of the fluidic gate causes the power stream to flow through the NOR output leg of the fluidic gate. The gas flow monitor apparatus provides a more reliable means for monitoring the ratio of respiratory gas to anesthetic gas, having fewer moving parts and occupying less space than was available in the prior art.

DISCUSSION OF THE PREFERRED EMBODIMENT

Figure 1:
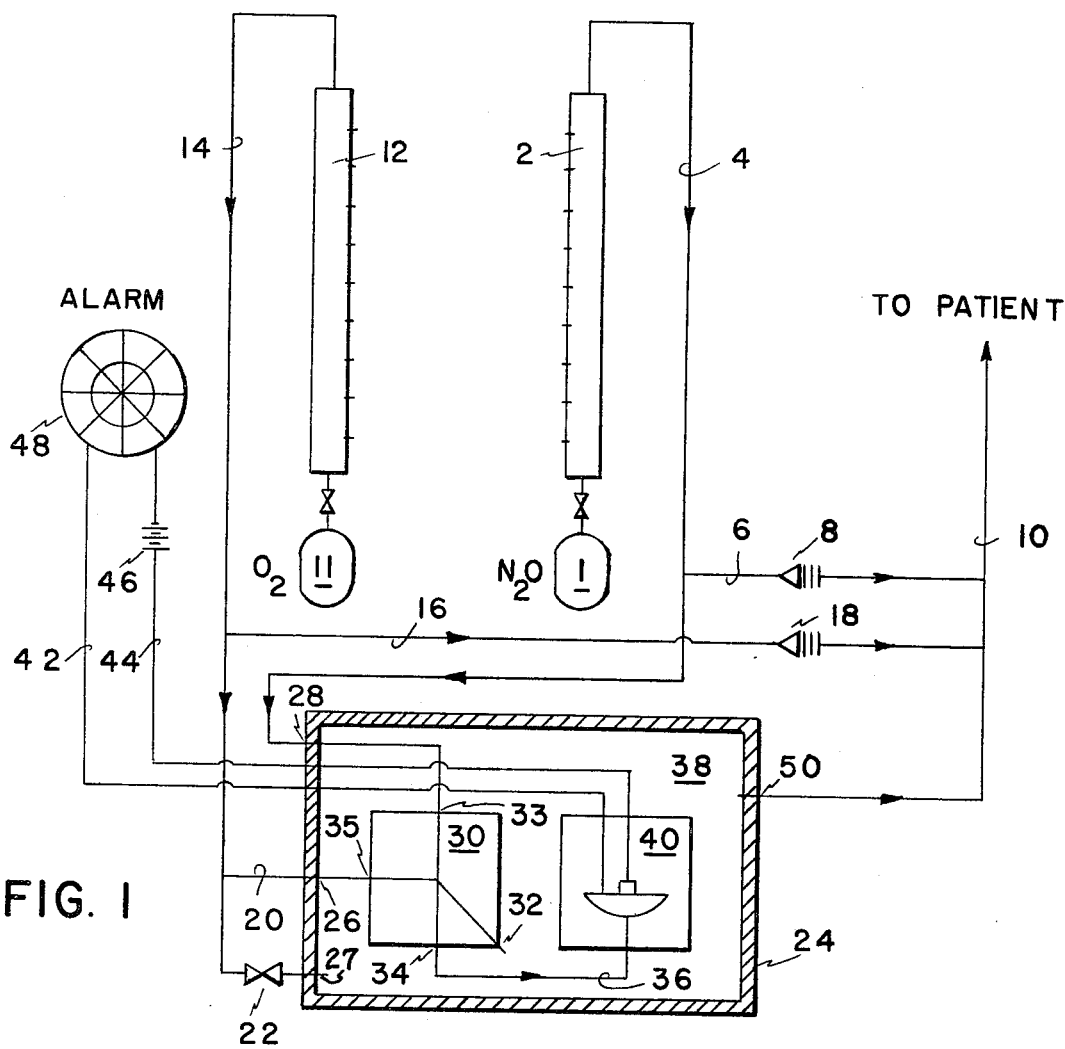
FIG. 1 depicts the gas flow monitor apparatus for anesthetic machines.

The gas flow monitor apparatus for anesthetic machines is shown in FIG. 1. The compressed gas cylinder 1 is the source of a pressurized anesthetic gas such as nitrous oxide. The flow meter 2 connected to gas cylinder 1, is connected, in turn, by means of the tubing 4, the bypass tubing 6, and the pop-off valve 8, to the breathing tube 10. The flow meter 12 controls the rate of flow of a respiratory gas, such as oxygen, supplied from the compressed gas cylinder 11 to the system. Flow meter 12 is connected by means of the tubing 14, the bypass tubing 16, and the pop-off valve 18, to the breathing tube 10. The resultant mixture of the anesthetic gas and the respiratory gas in the breathing tube 10 is administered to the patient under anesthesia.

The gas tight enclosure 24 is an enclosed compartment having walls which are relatively impervious to the anesthetic gas and the respiratory gas. Gas tight enclosure 24 has ingress ports 26, 27 and 28, and an egress port 50. Contained within the compartment of the gas tight enclosure 24 is an OR/NOR fluidic logic gate 30 and a pneumatically actuated electric switch 40.

Figure 2:
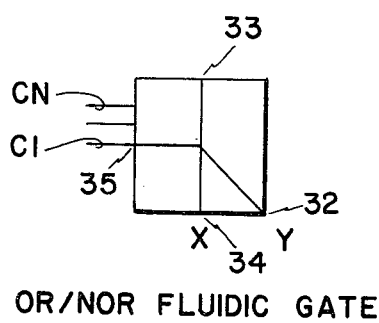
FIG. 2 illustrates the symbolic representation of an OR/NOR fluidic logic gate.

FIG. 2 illustrates a schematic representation of an OR/NOR fluidic logic gate. For the operation of this device, a gas supply must be connected at the power stream port 33. This supply is recovered at the OR output leg Y 32 if sufficient flow is present at any one of the control stream inputs, C1...CN, 35. Otherwise, the supply pressure is recovered at the NOR output leg X34. Thus, the Y port 32 may be considered logically as Y = C1 or C2 or ... or CN.

In the circuit of FIG. 1, the OR/NOR fluidic gate 30 is used with all but one of the control stream inputs $C_n$35 of FIG. 2, blocked. The output Y is called the OR leg 32 and the output X is called the NOR leg 34 of the gate.

Figure 3:
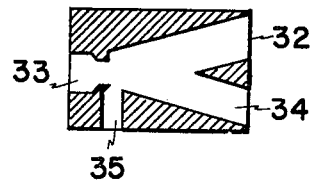
FIG. 3 depicts the structure of an OR/NOR fluidic logic gate.

FIG. 3 illustrates the physical configuration of the OR/NOR fluidic gate 30. In this device, the control stream port 35 is located on one side of the power stream jet 33. The asymmetrical design indicates that the gas flowing from the power stream jet 33 will attach to the side on which the control stream ports are positioned, in the absence of any flow of gas through the control stream 35. If sufficient gas flows in the control stream 35, gas flowing out of the power stream 33 will be deflected into the OR output leg 32. If no gas flows in the control stream 35, the gas flowing from the power stream 33 will flow out of the NOR leg 34. The operation of the OR/NOR fluidic logic device is based upon the Coanda Effect which is further described in E.F. Humphrey et al, Fluidics, Fluid Amplifier Assoc., Inc., 1965.

Returning to the circuit of FIG. 1, tubing 4 passes through the ingress port 28 and connects to the power stream input 33 of the OR/NOR fluidic device 30. Tubing 14 connects to the tubing 20 which passes through the ingress port 26 of the gas tight enclosure 24 and connects to the control stream input port 35 of the OR/NOR fluidic logic device 30. The OR output leg port 32 of the fluidic device 30 opens into the enclosed compartment 38 of the gas tight enclosure 24. The NOR output leg port 34 connects to the tubing 36 which, in turn, is connected to the pneumatic input port of the pneumatically actuated electric switch 40.

The pneumatically actuated electric switch 40 is normally an open electric circuit when there is no relative positive pressure on the input port connected to the tube 36. Wire 42 connects a first pole of the alarm means 48 to a first pole of the switch 40, the other pole of the alarm 48 being connected to the negative side of the battery 46. The positive side of the battery 46 is connected by means of wire 44 to the opposite pole of the switch 40. When a positive relative pressure is present in the tubing 36, the pneumatically actuated electric switch 40 closes the electric circuit formed by wire 42, the alarm 48, the battery 46, and wire 44, thereby energizing the alarm means 48.

A preset valve 22 is connected between the tubing 14 and the internal compartment 38 of the gas tight enclosure 24. The breathing tube 10 is connected through the egress port 50 to the internal compartment 38 of the gas tight enclosure 24.

The operation of the device prevents the anesthetic gas from the cylinder 1 from being accidentally turned on at the beginning of an operative procedure or prevents the respiratory gas from the cylinder 11 from being accidentally turned off at the end of an operative procedure while the anesthetic gas is still flowing. For example, if the nitrous oxide from the cylinder 1 is turned on at the beginning of an operative procedure, before the oxygen gas from the cylinder 11 is turned on, the nitrous oxide will flow through the tubing 4 to the power stream input port 33 of the fluidic gate 30. Since there is no oxygen flowing in at the control stream port 35, the fluidic gate 30 will direct the power stream into the NOR output leg 34, thereby pressurizing the tubing 36 and closing the pneumatically actuated electric switch 40, thereby setting off the alarm means 48.

Alternately, during the course of a normal operative procedure, oxygen flows from the cylinder 11 into the control stream input port 35 of the fluidic gate 30 at a sufficient rate to deflect the nitrous oxide flowing into the power stream input port 33, so as to cause the resulting mixture of nitrous oxide and oxygen to flow through the OR output leg 32 and into the internal compartment 38 of the gas tight enclosure 24. This gas mixture then flows out of gas tight enclosure 24 through the egress port 50 and into the breathing tube 10 to combine with the nitrous oxide and oxygen gasses supplied through the bypass tubes 6 and 16, respectively. There is no flow through the NOR output leg 34 and therefore no relative positive pressure in the tube 36 and hence the pneumatically actuated electric switch 24 maintains the open circuit condition and the alarm remains off.

When, during the course of an operative procedure where the nitrous oxide flowing from source 1 and the oxygen flowing from source 11 have been flowing at their proper flow rates, a malfunction occurs in the oxygen source 11 or the oxygen cylinders are inadvertantly spent, the following action occurs. The flow rate of the oxygen passing through tube 14, tube 20 and into the control stream input port 35 is reduced below the minimum threshold necessary to divert the flow of the nitrous oxide in the power stream 33 into the OR output leg 32. The fluidic gate then operates to direct the nitrous oxide from the power stream 33 into the NOR output leg 34, thereby pressurizing the tube 36 and closing the circuit in the pneumatically actuated switch 40. This circumstance causes the alarm 48 to sound, thereby alerting the anesthetist that an insufficiency in the oxygen supply has occurred and that corrective action must be immediately taken.

The preset valve 22 connecting the oxygen supply tube 14 to the interior compartment 38 of the gas tight enclosure 24, serves to preset the minimum at which the fluidic gate 30 will switch. This operation obtains since the preset valve 22 is connected in parallel with the control stream 35 and OR output leg 32 of the fluidic gate 30, between the oxygen supply tube 14 and the interior compartment 38 of the gas tight enclosure 24.

Fluidic components typically have a maximum operating pressure of approximately 10 lbs. per square inch. Thus 3 lb. per square inch pop-off valves 8 and 18 in the bypass lines 6 and 16, respectively may be used to allow extra flow to bypass the fluidic component 30. All gasses originating from the anesthetic source 1 and the respiratory source 11 ultimately flow to the breathing tube 10 or circuit.

For example, a typical pneumatically actuated electric switch 40 may require a minimum of 800 ml. per minute of nitrous oxide to close its circuit. The flow of oxygen required to prevent the pneumatically actuated electric switch 40 from closing and the alarm sounding, can be varied with the preset valve 22, but in this example will have a minimum flow rate of approximately 500 ml. per minute. For this example, a one liter per minute setting for the flow rate of the oxygen through the control stream port 35 has been found most practical. There is a small hysteresis around the set point for the switching of the fluidic gate 30 and a less than 10 per cent increase in it at high flow rates. With a one liter per minute setting for the oxygen flow rate, for example, the alarm 48 will sound if more than 800 ml. per minute of nitrous oxide and less than 1000 ml. per minute of oxygen are flowing.

The components of the fluidic system shown in FIG. 1 are compact and the entire assembly will fit into a cylinder 3 inches in diameter and 4 inches long.

It is seen that the pneumatically actuated electric switch 40 could have been located outside the compartment 38 of the gas tight enclosure 24. It is further recognized, that instead of using an electrically actuated alarm 48, a pneumatically actuated alarm driven by the nitrous oxide pressure from the source 1 can be employed. Alternately, a mechanical alarm actuated by the pressure from the tube 36 could be employed. The alarm 48, which is disclosed as electrically actuated, can be a light, a buzzer, or other means for calling the attention of the operator. It should be recognized that although the apparatus disclosed employed nitrous oxide as the anesthetic gas, other suitable gases such as cyclopropane or ethylene could be employed.

Although only one embodiment of the invention has been illustrated in the accompanying drawings and described in the foregoing specification, it should be understood by those skilled in the art that various changes such as in the relative dimensions of the parts, materials used, and the like, as well as the suggested manner of the use of the apparatus of the invention may be made therein without departing from the spirit and scope of the invention.

I claim:

1. In an anesthetic machine including a source of pressurized anesthetic gas and a source of pressurized respiratory gas, a gas flow monitor comprising:

A fluidic OR/NOR gate having a power stream input connected to said source of anesthetic gas and a control stream input connected to said source of respiratory gas and having an OR output leg and a NOR output leg;

A breathing circuit for a patient connected to said OR output leg of said fluidic gate;

Said anesthetic gas and said respiratory gas being mixed in said fluidic gate and the resulting gas mixture flowing through said OR output leg thereof and into said breathing circuit, when the flow rate of said respiratory gas in said control stream is sufficiently great;

An alarm means connected to said NOR output leg of said fluidic gate, for manifesting an alarm signal when a reduction in flow rate of said respiratory gas in said control stream causes said power stream to flow through said NOR output leg of said fluidic gate.

2. The apparatus of claim 1, which further comprises:

A pneumatically actuated switching means connected between said NOR output leg of said fluidic gate and said alarm means for actuating said alarm means.

3. The apparatus of claim 2, wherein said pneumatically actuated switching means closes an electrical circuit connected to said alarm means.

4. The apparatus of claim 1, wherein said breathing circuit further comprises:

A gas tight enclosure enveloping said fluidic gate and having first and second ingress ports through which the connections from said anesthetic gas source and said respiratory gas source pass to said power stream input and said control stream input, respectively of said fluidic gate and are hermetically sealed with said enclosure;

an egress port in said gas tight enclosure;

a breathing tube hermetically connected to said egress port of said gas tight enclosure;

said OR output leg of said fluidic gate outputting said resultant gas mixture to the interior of said gas tight enclosure;

a third ingress port in said gas tight enclosure;

a presetting valve connected between said source of respiratory gas and hermetically connected to said third ingress port and in parallel with said control stream input of said fluidic gate, for presetting the minimum flow of said respiratory gas at which said fluidic gate will switch when said anesthetic gas is flowing.

5. The apparatus of claim 4, which further comprises:

A first bypass supply tube connected between said source of pressurized anesthetic gas and said breathing tube, and in parallel with said gas tight enclosure, for providing a portion of anesthetic gas to said breathing tube;

A second bypass supply tube connected between said source of pressurized respiratory gas and said breathing tube, and in parallel with said gas tight enclosure, for providing a portion of respiratory gas to said breathing tube.

6. The apparatus of claim 5, which further comprises:

A first pop-off valve in said first bypass supply tube;

A second pop-off valve in said second bypass supply tube.

7. The apparatus of claim 1, wherein said anesthetic gas is nitrous oxide and said respiratory gas is oxygen.

8. The apparatus of claim 1, wherein said respiratory gas is taken from the group consisting of oxygen and air and said anesthetic gas is taken from the group consisting of nitrous oxide, ethylene, and cyclopropane.

* * * * *